United States Patent
Li

(10) Patent No.: US 10,355,310 B2
(45) Date of Patent: Jul. 16, 2019

(54) ELECTROLYTE COMPOSITIONS FOR ELECTROCHEMICAL DEVICES

(71) Applicant: SHENZHEN CAPCHEM TECHNOLOGY CO., LTD., Shenzhen (CN)

(72) Inventor: Wentao Li, Solon, OH (US)

(73) Assignee: SHENZHEN CAPCHEM TECHNOLOGY CO., LTD., Shenzhen (CN)

( * ) Notice: Subject to any disclaimer, the term of this patent is extended or adjusted under 35 U.S.C. 154(b) by 62 days.

(21) Appl. No.: 15/154,114

(22) Filed: May 13, 2016

(65) Prior Publication Data
US 2016/0351962 A1 Dec. 1, 2016

Related U.S. Application Data

(60) Provisional application No. 62/167,537, filed on May 28, 2015.

(51) Int. Cl.
| | |
|---|---|
| H01M 10/0567 | (2010.01) |
| H01M 10/0525 | (2010.01) |
| C07D 317/40 | (2006.01) |
| C07D 497/04 | (2006.01) |
| H01G 11/64 | (2013.01) |

(52) U.S. Cl.
CPC ...... *H01M 10/0567* (2013.01); *C07D 317/40* (2013.01); *C07D 497/04* (2013.01); *H01G 11/64* (2013.01); *H01M 10/0525* (2013.01); *H01M 2300/0025* (2013.01); *Y02E 60/13* (2013.01)

(58) Field of Classification Search
CPC ......... H01M 10/0525; H01M 10/0567; H01M 2300/0025; C07D 317/40; C07D 497/04
See application file for complete search history.

(56) References Cited

U.S. PATENT DOCUMENTS

| | | | | | |
|---|---|---|---|---|---|
| 4,178,329 | A | * | 12/1979 | Becker | A61L 33/064 525/77 |
| 5,610,314 | A | * | 3/1997 | Cheng | C07D 317/40 549/228 |
| 7,592,095 | B2 | * | 9/2009 | Lee | H01M 4/62 429/110 |
| 8,076,032 | B1 | * | 12/2011 | West | H01M 10/052 429/313 |
| 2002/0084445 | A1 | * | 7/2002 | Garbe | C07C 317/18 252/364 |
| 2003/0087161 | A1 | * | 5/2003 | Topsoe | H01M 10/0525 429/330 |
| 2007/0009803 | A1 | * | 1/2007 | Kim | H01M 2/145 429/251 |
| 2007/0059597 | A1 | * | 3/2007 | Nakanishi | C08G 77/04 429/188 |
| 2007/0231671 | A1 | * | 10/2007 | Inasaki | H01B 1/122 429/483 |
| 2009/0081557 | A1 | * | 3/2009 | Chen | H01M 4/382 429/337 |
| 2009/0087721 | A1 | * | 4/2009 | Yoshida | H01M 4/9083 429/422 |
| 2009/0280414 | A1 | * | 11/2009 | Koh | H01M 4/13 429/304 |
| 2011/0104565 | A1 | * | 5/2011 | Utsumi | H01M 2/127 429/200 |
| 2012/0082890 | A1 | * | 4/2012 | Dong | H01M 6/164 429/188 |
| 2013/0004862 | A1 | * | 1/2013 | Miyoshi | C07D 327/10 429/337 |
| 2013/0052542 | A1 | * | 2/2013 | Abraham | H01M 10/0525 429/332 |
| 2013/0234074 | A1 | * | 9/2013 | Gilles | B22F 1/0011 252/504 |
| 2014/0212770 | A1 | * | 7/2014 | Abe | H01M 10/0525 429/331 |
| 2014/0234696 | A1 | * | 8/2014 | Sakuma | H01M 10/0566 429/163 |
| 2014/0272607 | A1 | * | 9/2014 | Amine | H01M 10/052 429/338 |

FOREIGN PATENT DOCUMENTS

| | | | |
|---|---|---|---|
| DE | 1815946 | * | 7/1970 |
| JP | 59-025386 | * | 2/1984 |
| JP | 11-031526 | * | 2/1999 |
| JP | 2001-035530 | * | 2/2007 |
| WO | WO 2013/024717 | * | 2/2013 |

OTHER PUBLICATIONS

Machine translation of JP 2001-035530, published on Feb. 9, 2001 (Year: 2001).*
Translation of Table 1 in par.0044 of JP 2001-035530, published on Feb. 9, 2001 (Year: 2001).*
Machine translation of JP 11-031526, published on Feb. 2, 1999 (Year: 1999).*
Ishii, H., Yamada, N., Fuchigami, T.-Highly selective anodic monofluorination of 4-arylthio-1,3-dioxolan-2-ones: a marked solvent effect on product selectivity, Chem. Commun. 2000, 1617-1618 (Year: 2000).*
Ozaki, M., Matsuda, M., Tomii, Y., Kimura, K., Segawa, J., Kitano, M., Kise, M., Shibata, K., Otsuki, M., Nishino, T.—In Vivo Evaluation of NM441, a New Thiazeto-Quinoline Derivative. Antimicrobial Agents and Chemotherapy, Dec. 1991, pp. 2496-2499 (Year: 1991).*
Machine translation of JP 59-025386, published on Feb. 9, 1984 (Year: 1984).*

\* cited by examiner (Continued)

*Primary Examiner* — Anca Eoff

(57) ABSTRACT

Multi-functional additives containing at least one solid electrolyte interface (SEI) forming group and at least one SEI modifying group are advantageously employed in electrolyte compositions for electrochemical devices. The SEI forming group may comprise an organic carbonate moiety and the SEI modifying group may comprise a heteroatom functional group such as a sulfur containing organic moiety. The electrochemical devices include lithium ion batteries.

20 Claims, No Drawings

ELECTROLYTE COMPOSITIONS FOR ELECTROCHEMICAL DEVICES

This invention is aimed at additives for electrolyte compositions, electrolyte compositions containing the additives and electrochemical devices containing the additives. The electrolyte compositions are suitable for use in electrochemical devices such as lithium ion batteries.

Electrolyte compositions for use in lithium ion batteries typically contain a solvent and a lithium salt such as $LiPF_6$. Certain additives may be employed in the electrolyte compositions, for instance solid electrolyte interface (SEI) improvers, cathode protection agents, $LiPF_6$ stabilizers, overcharge protectors, flame retardants, Li deposition improvers, solvation enhancers, corrosion inhibitors, wetting agents and viscosity adjusting agents.

SEI related additives comprise two groups, SEI forming additives (SEI formers) and SEI modifying additives (SEI modifiers). Certain organic carbonate compounds serve as SEI forming additives. Certain other additives serve as SEI modifiers, such as sulfur containing compounds which improve high temperature performance. Such additives include 1,3-propane sultone. Currently, such additives are used alone or in combination.

There remains a need for electrolyte additives that further improve electrochemical cell performance.

Accordingly, disclosed is a class of additive compounds that are suitable for use in an electrochemical device. The compounds comprise at least one SEI forming functional group covalently bonded to at least one SEI modifying functional group.

DETAILED DISCLOSURE

The present multi-functional additive compound containing at least one SEI forming group and at least one SEI modifying group may be simply represented as (SEI forming group)$_n$-(bridge)$_m$-(SEI modifying group)$_p$ where
bridge is a hydrocarbylene,
m is 0, 1 or 2,
n is an integer from 1 to 10, for example from 1 to 5 or from 1 to 3,
p is an integer from 1 to 10, for example from 1 to 5 or from 1 to 3,
the SEI forming group comprises a chemical moiety capable of forming a solid electrolyte interface and
the SEI modifying group comprises a chemical moiety capable of modifying a solid electrolyte interface.

A suitable SEI forming group is for example an organic carbonate group, for instance a cyclic and/or unsaturated organic carbonate group.

Suitable SEI modifying groups are for example heteroatom functional groups containing one or more heteroatoms selected from the group consisting of S, P, Si, B and N.

Thus, present multi-functional additives may be represented as (organic carbonate group)$_n$-(bridge)$_m$-(heteroatom functional group)$_p$ where
bridge is a hydrocarbylene,
m is 0, 1 or 2,
n is an integer from 1 to 10, for example from 1 to 5 or from 1 to 3,
p is an integer from 1 to 10, for example from 1 to 5 or from 1 to 3 and
the heteroatom functional group contains one or more heteroatoms selected from the group consisting of S, P, Si, B and N.

The bonds represent covalent bonds. The SEI forming group may be directly covalently bonded to the SEI modifying group; or they may be covalently bonded together through a bridge group or groups. The SEI forming group is different than the SEI modifying group.

SEI film formation on the negative and/or positive electrode of a lithium ion battery helps protect the electrolyte composition. A suitable film is electronically insulating and allows transport of lithium ions. SEI modifying additives aid in improving battery cycle life, high temperature performance, and/or low temperature performance.

An organic carbonate group contains a following carbonate moiety.

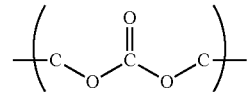

The open valences of the carbonate moiety together are hydrocarbylene and may form a ring; at least one open valence is bonded to the bridge group (or directly to the heteroatom functional group when m=0) and the other to a hydrogen or hydrocarbyl. Alternatively both open valences are bonded to two bridging groups. For example, the open valences may each be bonded to a methylene group. The terminal carbon atoms of the moiety are satisfied with bonds to hydrogen and/or hydrocarbyl.

When the open valences together form a ring, a carbon of the ring is covalently bonded to the bridge group(s) and the bridge group(s) are covalently bonded to the heteroatom functional group. It is also possible for more than one carbon of the ring to be covalently bonded to the bridge group.

The organic carbonate group is cyclic or acyclic and is saturated or is unsaturated.

For example, present additives may contain a carbonate group such as vinylene carbonate (VC), ethylene carbonate (EC), methyl vinylene carbonate (MVC), dimethyl vinylene carbonate, allyl ethyl carbonate (AEC), vinyl ethylene carbonate (VEC), methylene ethylene carbonate (MEC), propylene carbonate (PC), trimethylene carbonate, 1,2-butylene carbonate (BC), dimethyl carbonate (DMC), diethyl carbonate (DEC), ethylmethyl carbonate (EMC), dipropyl carbonate, difluoroethylene carbonate, monofluoroethylene carbonate, dichloroethylene carbonate or monochloroethylene carbonate.

Respectively, present additives may contain one or more carbonate groups such as the following.

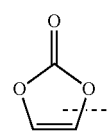

(1)

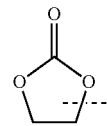

(2)

(3) 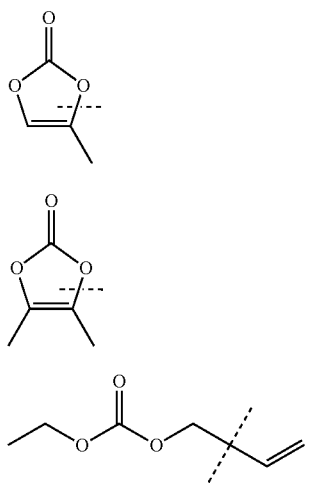

(4)

(5)

(6) 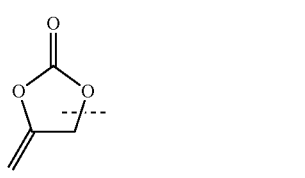

(7)

(8) 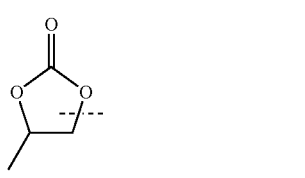

(9) 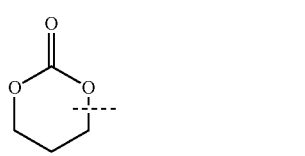

(10) 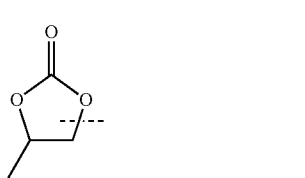

(11) 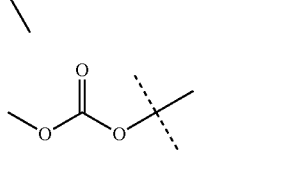

(12) 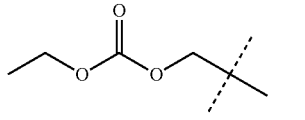

(13) 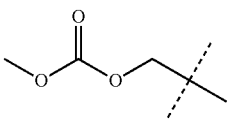

(14) 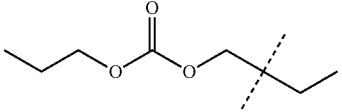

(15) 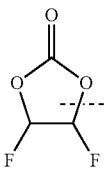

(16) 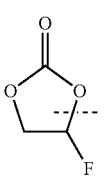

(17) 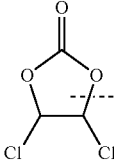

(18) 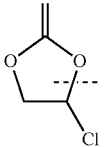

The dashed line represents a covalent bond between the organic carbonate group and the hydrocarbylene bridge group. When "m" is 0, there is no bridge group and the dashed line is a covalent bond directly linking an organic carbonate group and a heteroatom functional group. When "m" is 2, there are two dashed lines and both are covalently bonded to a heteroatom functional group via for example 2 bridging groups. The dashed line or lines is bonded to any carbon atom of the organic carbonate group containing a C—H bond and replacing said C—H bond.

When the carbonate moiety is part of a ring system, the carbonate group is "cyclic". When the carbonate group contains any unsaturated carbon carbon bonds, it is "unsaturated". Vinylene carbonate, vinyl ethylene carbonate and methylene ethylene carbonate are cyclic, unsaturated organic carbonate groups. Ethylene carbonate is a cyclic, saturated group. Allyl ethyl carbonate is an acyclic, unsaturated group. Dimethyl carbonate is an acyclic, saturated carbonate group.

The hydrocarbylene bridge group, when present, is covalently bonded to the organic carbonate group and to the heteroatom functional group. When the hydrocarbylene bridge group is not present, the organic carbonate group and heteroatom functional group are directly covalently bonded together.

The functional groups advantageously contain heteroatom moieties selected from the group consisting of
sulfonates, sulfates, sulfites, sulfones, sulfoxides or thio groups;
phosphates, phosphinates, phosphonates, phosphine oxides, phosphites, phosphonites, phosphinites or phosphines;
siloxanes, silyl ethers or silanes;
borates, boronic esters, borinic esters or boranes;
amines or amides; and
bis-sulfonylimides.

The sulfonate, sulfate, sulfite, sulfone, sulfoxide and thio moieties are respectively —S(O)$_2$O—, —OS(O)$_2$O—, —OS(O)O—, —S(O)$_2$—, —S(O)— and —S—.

The phosphate, phosphinate, phosphonate, phosphine oxide, phosphite, phosphonite, phosphinite and phosphine moieties are respectively —O—P(O)(OR)O—, —O—P(O)(R)— or —P(O)(OR)—; —O—P(O)(OR)— or —O—P(O)(R)—O—; —P(O)(R)—, —O—P(OR)—O—, —O—P(OR)— or —O—P(R)—O—; —P(OR)— or —O—P(R)—; and —P(R)—.

The siloxane moiety is —(R)(R)Si—O—Si(R)(R)—, the silyl ether moieties include derivatives of silanols, silane diols and silane triols represented as —Si(R)(OR)—, —O—Si(R)(R)—, —Si(OR)(OR)—, —O—Si(R)(OR)—, —O—Si(R)(R)—O—, —Si(OR)(OR)—O— and —O—Si(R)(OR)—O—; and the silane moiety is —Si(R)(R)—.

The boronic ester moiety is —B(OR)—O— or is —O—B(R)—O—; borinic ester is —B(R)—O— or is —B(OR)—; and the borate and borane moieties are respectively —O—B(OR)—O— and —B(R)—.

The amide moiety is —C(O)N(R)— and the amine moiety is —N(R)—.

The bis-sulfonylimide moiety is —S(O)$_2$—NR'—S(O)$_2$—.

The open valences of the heteroatom moieties together are hydrocarbylene and form a ring; or alternatively, one open valence is bonded to the bridge group (or carbonate group when m=0) and the other to a hydrogen or hydrocarbyl.

When the open valences together form a ring, a carbon atom of the hydrocarbylene ring is covalently bonded to the bridge group(s) or the organic carbonate group.

The heteroatom functional group is also cyclic or acyclic and is saturated or unsaturated.

The functional group containing one or more heteroatoms is also generally organic, containing at least one carbon atom.

R is independently hydrogen or hydrocarbyl.

R' is hydrogen, hydrocarbyl or an alkali metal.

For instance, present additives may contain one or more heteroatom functional groups such as 1,3-propane sultone, 1,4-butyl sultone, ethylene sulfite, ethylene sulfate, propylene sulfate, butylene sulfate, pentylene sulfate, vinylene sulfite, trimethylene sulfite, 1,3-propanediol cyclic sulfate, prop-1-ene-1,3-sultone, propylene sulfite or 1,5,2,4-dioxadithiane-2,2,4,4-tetraoxide.

Respectively, present additives may contain one or more heteroatom functional groups such as the following.

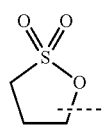

(50)

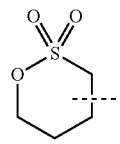

(51)

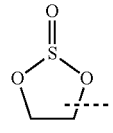

(52)

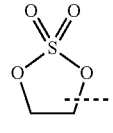

(53)

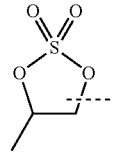

(54)

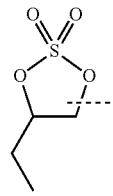

(55)

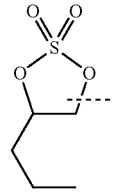

(56)

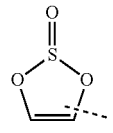

(57)

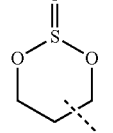

(58)

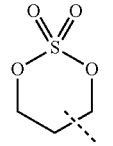

(59)

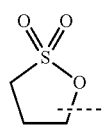

(60)

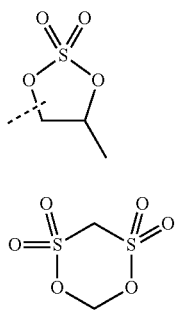
(61)

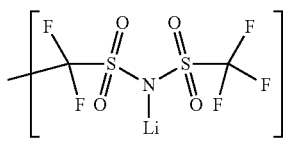
(62)

The dashed line represents a covalent bond between the heteroatom functional group and the hydrocarbylene bridge group. Again, when "m" is 0, there is no bridge group and the dashed line is a covalent bond directly linking a functional group and an organic carbonate group. When "m" is 2, there will be two dashed lines and the dashed lines are bonded to any carbon atom of the heteroatom functional group containing a C—H bond and replacing said C—H bond.

Other suitable heteroatom functional groups include the following.

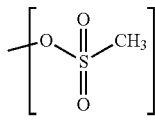
(63)

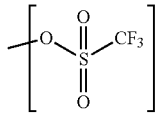
(64)

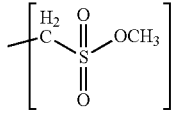
(65)

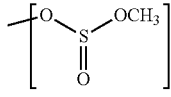
(66)

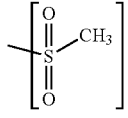
(67)

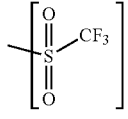
(68)

(69)

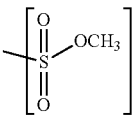
(70)

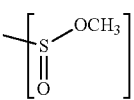
(71)

Hydrocarbyl is any straight or branched chain, cyclic or acyclic hydrocarbon based group.

Hydrocarbyl is for instance alkyl, alkenyl, cycloalkyl, cycloalkenyl, aryl or aralkyl, which may be substituted by one or more groups selected from the group consisting of halogen, hydroxy, $C_1$-$C_4$alkoxy, thio, $C_1$-$C_4$alkylthio, amino, $C_1$-$C_4$alkylamino, di-$C_1$-$C_4$alkylamino, nitro, cyano, —COOH and —COO⁻. Hydrocarbyl may also be interrupted by one or more groups selected from the group consisting of —O—, —S—, —NH— and —N($C_1$-$C_4$alkyl)-. Hydrocarbyl may be both substituted by one or more of said groups and interrupted by one or more of said groups. For instance alkyl, alkenyl, cycloalkyl, cycloalkenyl, aryl or aralkyl may be substituted by one to three groups selected from the group consisting of chloro, fluoro, hydroxy, methoxy, ethoxy, propoxy, butoxy, thio, methylthio, methylamino, ethylamino, propylamino, butylamino, dimethylamino, diethylamino, dipropylamino, dibutylamino, —COOH, —COO⁻, cyano and nitro and/or may be interrupted by one to three groups selected from the group consisting of —O—, —S—, —NH— and —N($C_1$-$C_4$alkyl)-.

Hydrocarbyl also includes polyethylene glycols and polypropylene glycols such as R'(OC$_2$H$_4$)$_n$— or R'(OC$_3$H$_6$)$_n$— where R' is hydrogen or alkyl and n is an integer from 1 to 50, for instance from 1 to 40, 1 to 30 or 1 to 20, for instance from 1 to 10. When the bridge group contains an ethylene glycol or propylene glycol unit, the bridge is an oxyalkylene. Oxyalkylene also includes any alkylene containing one or more oxy atoms.

The bridge group is a hydrocarbylene. Hydrocarbylene is a divalent version of hydrocarbyl. Hydrocarbylene is for instance methylene (—CH$_2$—), ethylene (—CH$_2$CH$_2$—), vinylene (—CH═CH—), trimethylene (—CH$_2$CH$_2$CH$_2$—), through two covalent bonded methylene group (to form a cyclic connection as in 6 of the examples) and the like.

Alkyl is for instance from 1 to 25 carbon atoms, is branched or unbranched and includes methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, icosyl and docosyl.

Alkenyl is an unsaturated version of alkyl, for instance allyl.

Cycloalkyl includes cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl.

Cycloalkenyl is an unsaturated version of cycloalkyl.

Aryl includes phenyl, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

Aralkyl includes benzyl, α-methylbenzyl, α,α-dimethylbenzyl and 2-phenylethyl.

Halogen is F, Cl, Br or I.

Alkali metals include Li, Na and K.

For instance, present additives include the following.

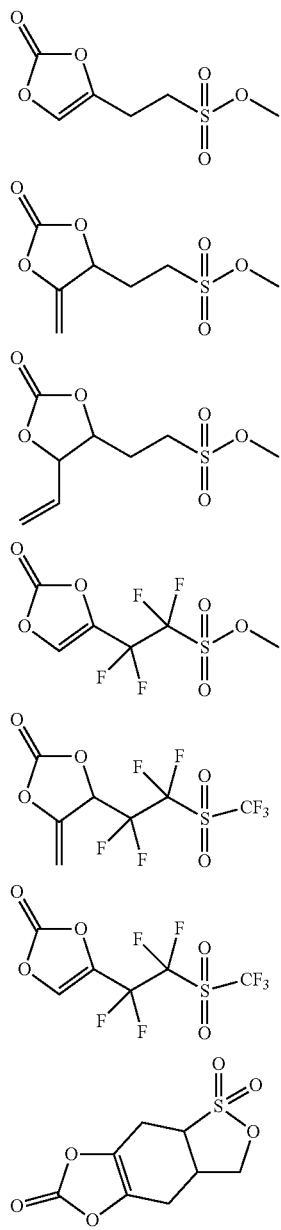

In these additives, the organic carbonate group is vinylene carbonate, methylene ethylene carbonate or vinyl ethylene carbonate. The heteroatom functional group is $-S(O)_2OCH_3$ or is $-S(O)_2CF_3$. The bridge group or groups are $-(CH_2CH_2)-$ or $-(CF_2CF_2)$.

Present additives also include for example the following.

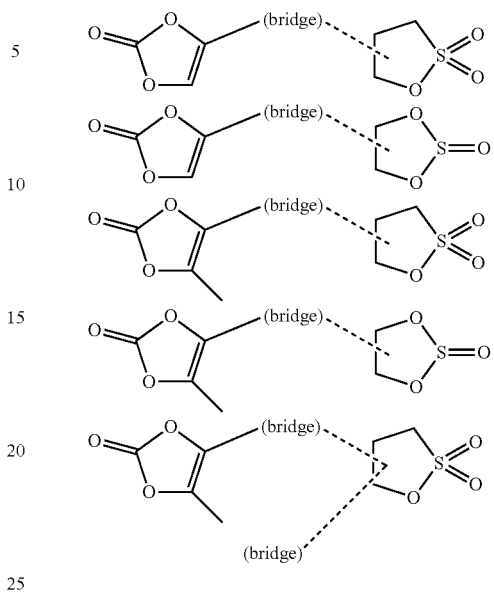

Present additives may be prepared via traditional organic synthesis techniques. Such techniques are taught for instance in U.S. Pub. No. 2014/0193707 and are shown in the instant Examples.

The functions of the multi-functional additives include SEI stabilization, prevention of metal deposition and prevention of solvent reduction. The present additives will improve cell performance.

The electrolyte compositions are suitable for use in a variety of electrochemical devices.

The present electrolyte compositions are generally anhydrous, typically containing ≤20 ppm water, for instance ≤19, ≤18, ≤17, ≤16, ≤15, ≤14, ≤13, ≤12, ≤11, ≤10, ≤9, ≤8, ≤7, ≤6, ≤5 or ≤4 ppm water by weight, based on the total weight of the electrolyte composition.

Electrochemical devices include primary lithium batteries, rechargeable lithium ion batteries, double layer capacitors, lithium ion capacitors, solar cells, electrochromic displays, sensors and biosensors.

Rechargeable lithium ion batteries (cells) comprise an anode capable of intercalating and disintercalating lithium ions, a cathode and a non-aqueous electrolyte solution of a lithium salt in an organic solvent. The electrodes are in contact with the electrolyte and are separated by a separator.

Cathode active materials include one or more compounds selected from the group consisting of lithium cobalt oxide, lithium nickel cobalt manganese oxide (NCM, $LiNi_xMn_y$-$Co_zO_2$), lithium manganese oxide (LMO, $LiMn_2O_4$), lithium nickel oxide and lithium iron phosphate (LFP, $LiFePO_4$).

Anode active materials include carbon and graphitic materials such as natural graphite, artificial graphite, expanded graphite, graphene, carbon fiber, non-graphitizable carbon, carbon black, carbon nano tube, fullerene and activated carbon; metals alloyable with lithium such as Al, Si, Sn, Ag, Bi, Mg, Zn, In, Ge, Pb, Pd, Pt and Ti and compounds including such elements; composite materials of the metals or their compounds and the carbon or graphite materials; and lithium-containing nitrides. For example, crystalline carbon, amorphous carbon, silicon-based active materials, tin-based active materials, silicon-carbon-based active materials and mixtures thereof may be employed as anode active materials.

In addition to the cathode and anode active materials, the electrodes may further include binders and/or conductive materials and/or other additives. The electrode assemblies may include these mixtures in adherence to a current collector such as a metal foil.

The binder assists in coupling the active material and the conductive material and the mixture to the current collector. Binders include poly(tetrafluoroethylene) (PTFE), a copolymer of acrylonitrile and butadiene (NBR), polyvinylidene fluoride (PvDF), polyvinyl alcohol, carboxy methyl cellulose (CMC), starch, hydroxy propyl cellulose, regenerated cellulose, polyvinylpyrrolidone, tetrafluoroethylene, polyethylene, polypropylene, ethylene-propylene-diene polymer (EPDM), sulfonated-EPDM, styrene-butadiene rubber (SBR), fluorine rubber, copolymers thereof and mixtures thereof. Binders may be employed from about 1 to about 50 weight %, based on the total weight of electrode assembly.

Conductive materials may be from about 1 to about 20 weight %, based on the total weight of the electrode assembly. Conductive materials include graphitic materials such as natural graphite, artificial graphite, a carbon black such as acetylene black, Ketjen black, channel black, furnace black or lamp black, conductive fibers such as carbon fiber or metal fiber, metal powders such as carbon fluoride, aluminum or nickel powder, conductive metal oxides such as zinc oxide, potassium titanate or titan oxide and other conductive materials such as polyphenylene derivatives.

A filler may be employed as a component for controlling expansion of the anode. Fillers include olefin-based polymers such as polyethylene or polypropylene and fibrous material such as glass fiber or carbon fiber.

A separator is interposed between the cathode and the anode which is for instance an insulating thin film ensuring high ion transmission. The separator generally has a pore size of about 0.01 to about 10 microns and a thickness of about 5 to about 300 microns. Separator materials include sheets or non-woven fabrics comprising materials including glass fiber, cotton, nylon, polyester, polyethylene, polypropylene, polyvinyl chloride, polytetrafluoroethylene and kraft paper.

The lithium secondary battery may for example be a coin-type battery having a cathode, an anode and a single-layer or multi-layer separator or a cylindrical or angled battery having a cathode, an anode and a roll-type separator.

The cathode may be prepared by mixing cathode active material with conductive material and/or a binder and a solvent, coating a metal foil with the mixture and heating and rolling. The anode may be prepared by mixing anode active material with a binder and solvent, coating a metal foil with the mixture and heating and rolling.

The lithium secondary battery according to the present invention may be prepared by inserting an electrode group having a cathode and an anode into a battery case and injecting the non-aqueous electrolyte solution of the present invention into the case. The battery case may have a metal can shape or a pouch shape made of metal laminate.

The organic solvent typically comprises one or more solvents selected from the group consisting of organic carbonates, sulfones, sulfoxides, esters, lactones, ethers and glymes.

The organic solvent may consist essentially or consist of one or more organic carbonates.

Organic carbonates are cyclic or acyclic and include ethylene carbonate (EC), propylene carbonate (PC), trimethylene carbonate, 1,2-butylene carbonate (BC), dimethyl carbonate (DMC), diethyl carbonate (DEC), ethylmethyl carbonate (EMC), dipropyl carbonate, vinylene carbonate, difluoroethylene carbonate and monofluoroethylene carbonate.

Sulfones and sulfoxides include methylsulfonylmethane (MSM or dimethylsulfone), ethylmethylsulfone, sulfolane and dimethylsulfoxide (DMSO).

Esters and lactones include γ-butyrolactone (GBL), γ-valerolactone, δ-valerolactone, ethyl acetate (EA), 2-methoxyethyl acetate, 2-ethoxyethyl acetate, 2-butoxyethyl acetate, 2-(2-butoxyethoxy)ethyl acetate (diethylene glycol butyl ether acetate, DBA), ethylene glycol diacetate (EGDA), ethyl propionate, propyl propionate, 3-ethoxy ethyl propionate (EEP), methyl butyrate (MB), n-amyl acetate (NAAC), propylene glycol methyl ether acetate (PMA), ethyl butryate (EB), diethyl malonate, dimethyl malonate and dibasic ester mixture (DBE).

Ethers and glymes include dimethoxymethane (DMM), diethoxymethane, 1,2-dimethoxyethane (DME or ethyleneglycol dimethylether or glyme), diglyme, triglyme, tetraglyme, ethyleneglycol diethylether (DEE), ethyleneglycol dibutylether, diethyleneglycol diethylether, tetrahydrofuran (THF), 2-methyltetrahydrofuran (2-MeTHF), 1,3-dioxane, 1,3-dioxolane (DIOX), 4-methyl-1,3-dioxolane (4-MeDIOX), 2-methyl-1,3-dioxolane (2-MeDIOX), 1,4-dioxane, dimethylether, ethylmethylether, diethylether, di-n-butylether, di-t-butylether, di-isopropylether, methyl-t-butylether, ethyl-t-butylether and t-amyl-methylether.

For example, at least two different solvents are advantageously used in combination, such as a combination of cyclic carbonate and linear carbonate, a combination of cyclic carbonate and lactone, a combination of cyclic carbonate, lactone and ester, a combination of cyclic carbonate, linear carbonate and lactone, a combination of cyclic carbonate, linear carbonate and ether or a combination of cyclic carbonate, linear carbonate and linear ester. Among them, a combination of cyclic carbonate and linear carbonate or a combination of cyclic carbonate, lactone and ester is preferred. A weight:weight ratio of cyclic carbonate(s) to linear carbonate(s) is for example from about 1:9 to about 7:3.

For example, the organic solvent contains a cyclic carbonate such as ethylene carbonate or propylene carbonate and one or more linear carbonates selected from dimethyl carbonate, ethylmethyl carbonate and diethyl carbonate. For example, the organic solvent comprises ethylene carbonate, ethylmethyl carbonate and diethyl carbonate.

The electrolyte compositions comprise one or more suitable lithium salts. Lithium salts include $LiPF_6$, $LiClO_4$, $LiN(CF_3SO_2)_2$, $LiAsF_6$, $LiCF_3SO_3$ and $LiBF_4$. For example, the electrolyte compositions contain $LiPF_6$. The lithium salts are generally employed in the organic solvent at a level of from about 0.5 mol/L (M) to about 2.5 M, from about 0.5 M to about 2.0 M, from about 0.7 M to about 1.6 M or from about 0.8 M to about 1.2 M.

Present additives, in total, are employed for example from about 0.01% to about 15% by weight, based on the total weight of the electrolyte composition. For example, these additives in total may be present from about 0.1 to about 12%, from about 0.2 to about 10%, from about 0.3 to about 8%, from about 0.4 to about 7% or from about 0.5 to about 5% by weight, based on the total weight of the electrolyte composition.

Present additives, in total, may be present at levels of about 0.6, about 0.8, about 0.9, about 1.0, about 1.1, about 1.2, about 1.4, about 1.6, about 1.8, about 2.0, about 2.2, about 2.4, about 2.6, about 2.8, about 3.0, about 3.2, about 3.4, about 3.6, about 3.8, about 4.0, about 4.2, about 4.4, about 4.6, about 4.8 or about 5.0 percent by weight, based on the total weight of the electrolyte composition.

The electrolyte compositions of the invention may advantageously comprise one or more further additives selected from the group consisting of solid electrolyte interface improvers, cathode protection agents, $LiPF_6$ stabilizers, overcharge protectors, flame retardants, Li deposition improvers, solvation enhancers, corrosion inhibitors, wetting agents and viscosity adjusting agents.

For instance, the electrolyte compositions may further contain one or more further additives selected from the group consisting of formulae (101) to (112)

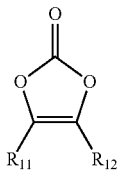  (101)

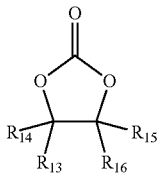  (102)

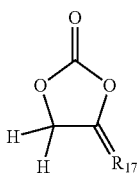  (103)

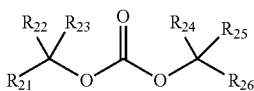  (104)

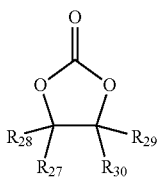  (105)

  (106)

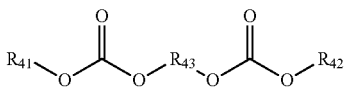  (107)

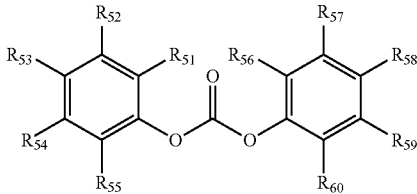  (108)

$Li_2PO_3F$ (lithium monofluorophosphate)  (109)

$LiPO_2F_2$ (lithium difluorophosphate)  (110)

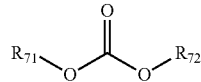  (111)

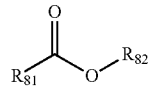  (112)

where $R_{11}$ and $R_{12}$ are independently hydrogen, halogen, alkyl or haloalkyl;

$R_{13}$, $R_{14}$, $R_{15}$ and $R_{16}$ are independently hydrogen, halogen, alkyl, haloalkyl, vinyl or allyl, where at least one of $R_{13}$ to $R_{16}$ is vinyl or allyl;

$R_{17}$ is hydrogen or alkyl;

$R_{21}$ to $R_{26}$ are independently hydrogen, halogen, alkyl or haloalkyl, where at least one of $R_{21}$ to $R_{26}$ is halogen or haloalkyl;

$R_{27}$ to $R_{30}$ are independently hydrogen, halogen, alkyl or haloalkyl, where at least one of $R_{27}$ to $R_{30}$ is halogen or haloalkyl;

$R_{31}$ is an optionally substituted $C_1$-$C_6$ alkylene, an optionally substituted $C_2$-$C_6$ alkenylene or an optionally substituted cycloalkylene, A is C=O, SO or $SO_2$, n is 0 or 1 and X is oxygen (O) or sulfur (S);

$R_{41}$ and $R_{42}$ are independently an optionally substituted $C_1$-$C_6$alkyl, an optionally substituted $C_2$-$C_6$alkenyl or an optionally substituted $C_2$-$C_6$alkynyl and $R_{43}$ is an optionally substituted $C_1$-$C_6$alkylene, an optionally substituted $C_2$-$C_6$alkenylene, an optionally substituted $C_2$-$C_6$alkynylene or an optionally substituted cycloalkylene, where the substituent is for instance halogen or $C_1$-$C_6$alkyl;

$R_{51}$ to $R_{60}$ independently are an optionally substituted $C_1$-$C_{18}$alkyl, alkenyl, alkynyl, alkoxy or alkylamino, or two of $R_{51}$-$R_{60}$ together are hydrocarbylene, where the substituent is for instance halogen atom or $C_1$-$C_6$alkyl;

$R_{71}$ and $R_{72}$ are independently alkyl or haloalkyl; and $R_{81}$ and $R_{82}$ are independently alkyl.

For example, suitable further additives include vinylene carbonate (1,3-dioxol-2-one), 4-vinyl-1,3-dioxolan-2-one, 4-fluoro-1,3-dioxolan-2-one, methylene ethylene carbonate, 1,3-propane sultone, 1,4-butyl sultone, prop-1-ene-1,3-sultone, 4-methyl-1,3,2-dioxathiolane-2-oxide and 1,5,2,4-dioxadithiane-2,2,4,4-tetraoxide.

Further additives also include one or more ionic compounds selected from the group consisting of ionic liquids. Ionic liquids are ionic compounds that exhibit a melting point of ≤150° C. or ≤100° C.

For instance, ionic liquids contain a cation selected from the group consisting of formulae (a)-(h)

  (a)

  (b)

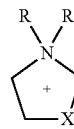  (c)

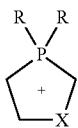

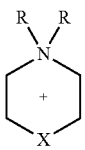

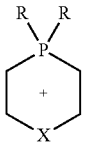

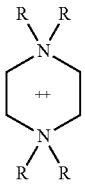

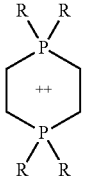

where
each R is independently H or $C_1$-$C_{16}$alkyl, for instance methyl, ethyl or propyl,
X is $CH_2$, O, S or NR where R is H or $C_1$-$C_{16}$alkyl, for instance H, methyl, ethyl or propyl and contain an anion selected from the group consisting of $[F_zB(C_mF_{2m+1})_{4-z}]^-$,
$[F_yP(C_mF_{2m+1})_{6-y}]^-$,
$[(C_mF_{2m+1})_2P(O)O]^-$,
$[C_mF_{2m+1}P(O)O_2]^{2-}$,
$[O-C(O)-C_mF_{2m+1}]^-$,
$[O-S(O)_2-C_mF_{2m+1}]^-$,
$[N(C(O)-C_mF_{2m+1})_2]^-$,
$[N(S(O)_2-C_mF_{2m+1})_2]^-$,
$[N(C(O)-C_mF_{2m+1})(S(O)_2-C_mF_{2m+1})]^-$,
$[N(C(O)-C_mF_{2m+1})(C(O)F)]^-$,
$[N(S(O)_2-C_mF_{2m+1})(S(O)_2F)]^-$,
$[N(S(O)_2F)_2]^-$,
$[C(C(O)-C_mF_{2m+1})_3]^-$,
$[C(S(O)_2-C_mF_{2m+1})_3]^-$,

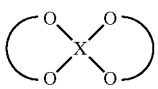 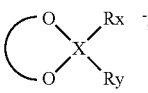 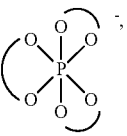

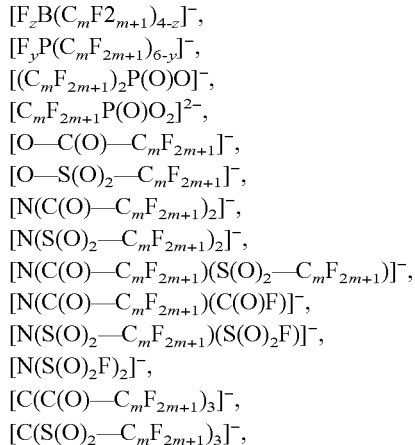

where
y is an integer of 1 to 5 and m is an integer of 1 to 8, for instance 1 to 4,
where any one $CF_2$ group may be replaced by O, $S(O)_2$, NR or $CH_2$,
where O⌒O is independently a bidentate group derived from the —OH groups of a 1,2- or 1,3-diol, a 1,2- or 1,3-dicarboxylic acid or from a 1,2- or 1,3-hydroxycarboxylic acid,
X is B or Al,
$R_w$, $R_x$, $R_y$ and $R_z$ are independently halogen, $C_1$-$C_{20}$perfluoroalkyl, $C_1$-$C_{20}$alkoxy, $C_1$-$C_{20}$alkoxy which is partly or fully fluorinated, $C_1$-$C_{20}$alkyl-COO, $C_1$-$C_{20}$alkyl-COO which is partly or fully fluorinated.

Cations of ionic liquids include ammonium and phosphonium ions. Ammonium ions include imidazolium and pyrrolidinium. For instance 1-ethyl-3-methylimidazolium, 1-hexyl-3-methylimidazolium, 1-butyl-1-methylpyrrolidinium or trihexyl(tetradecyl)phosphonium.

Anions of ionic liquids include carboxylates, imides, methides, borates, phosphates, sulfonates and aluminates. For instance, included are $F_2P(C_2F_5)_4^-$, $F_3P(C_2F_5)_3^-$, $F_4P(C_2F_5)_2^-$, $F_2P(C_3F_7)_4^-$, $F_3P(C_3F_7)_3^-$, $F_4P(C_3F_7)_2^-$, $F_2P(C_4F)_4^-$, $F_3P(C_4F_9)_3^-$, $F_4P(C_4F_9)_2^-$, perfluoroalkylcarboxylate, perfluoroalkylsulfonate, bis(perfluoroalkylsulfonyl)imide, (perfluoroalkylsulfonyl)(perfluoroalkylcarboxyl)imide, tris(perfluoroalkylsulfonyl)methide, trifluoroacetate, trifluoromethanesulfonate (triflate), bis(trifluoromethylsulfonyl)imide, tris(trinfluoromethylsulfonyl)methide, spiro-oxo borates and spiro-oxo phosphates, for example bisoxalatoborate (BOB), difluorooxalatoborate (dFOB), di(trinfluoroacetato)oxalatoborate (d(Ac)OB), trisoxalatophosphate, tetrafluorooxalatophosphate or di(trifluoroacetato)oxalatoaluminate.

Ionic liquids are also described for example in U.S. Pub. Nos. 2011/0045359 and 2014/0193707.

These further additives are for example employed at a level of from about 0.01% to about 15% by weight, based on the total weight of the electrolyte composition. For example, further additives may be employed from about 0.1 to about 10%, from about 0.2 to about 7% or from about 0.3 to about 5%, by weight, in total, based on the total weight of the electrolyte composition.

Further additives may be employed at a level, in total, of about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4 or about 2.5 percent by weight, based on the total weight of the electrolyte composition.

Also subject of the present invention are the multifunctional additive compounds and the electrochemical devices.

U.S. Patents, U.S. published patent applications and U.S. patent applications discussed herein are each hereby incorporated by reference.

The articles "a" and "an" are used herein to refer to one or to more than one (i.e., to at least one) of the grammatical object of the article. For example, "an organic carbonate group" means one carbonate group or more than one carbonate group.

Any ranges cited herein are inclusive.

The terms "substantially" and "about" used throughout this specification are used to describe and account for small fluctuations. For example, they can refer to less than or equal to ±5%, such as less than or equal to ±2%, less than or equal to ±1%, less than or equal to ±0.5%, less than or equal to ±0.2%, less than or equal to ±0.1% or less than or equal to ±0.05%. All numeric values herein are modified by the term "about," whether or not explicitly indicated. A value modified by the term "about" of course includes the specific value. For instance, "about 5.0" must include 5.0.

Following are some embodiments of the invention.

E1. An electrolyte composition suitable for use in an electrochemical device, which composition comprises a multi-functional additive compound containing an SEI forming group and an SEI modifying group; for example a multi-functional additive containing an organic carbonate group covalently bonded to a heteroatom functional group.

E2. A composition according to embodiment 1 where the additive is of formula (SEI forming group)$_n$-(bridge)$_m$-(SEI modifying group)$_p$ where
bridge is a hydrocarbylene,
m is 0, 1 or 2,
n is an integer from 1 to 10, for example from 1 to 5 or from 1 to 3,
p is an integer from 1 to 10, for example from 1 to 5 or from 1 to 3,
the SEI forming group comprises a chemical moiety capable of forming a solid electrolyte interface and
the SEI modifying group comprises a chemical moiety capable of modifying a solid electrolyte interface;
for example where the additive is of formula (organic carbonate group)$_n$-(bridge)$_m$-(heteroatom functional group)$_p$ where
the organic carbonate group contains a carbonate moiety and
the heteroatom functional group contains one or more heteroatoms selected from the group consisting of S, P, Si, B and N.

E3. A composition according to embodiments 1 or 2 where the SEI forming group is an organic carbonate group which contains a moiety

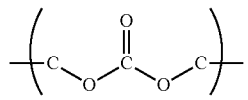

where the open valences together are hydrocarbylene and form a ring, which ring is bonded to the bridge group or the heteroatom functional group; or one open valence is bonded to the bridge group or to the heteroatom functional group and the other to a hydrogen or hydrocarbyl.

E4. A composition according to embodiment 3 where the organic carbonate group is cyclic.

E5. A composition according to embodiment 3 where the organic carbonate group is acyclic.

E6. A composition according to any of embodiments 3 to 5 where the organic carbonate group is unsaturated.

E7. A composition according to any of embodiments 3 to 5 where the organic carbonate group is saturated.

E8. A composition according to embodiment 3 where the organic carbonate group is cyclic and unsaturated.

E9. A composition according to any of the preceding embodiments where the organic carbonate group is selected from the group consisting of formulae (1)-(18)

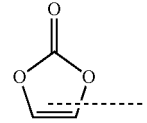 (1)

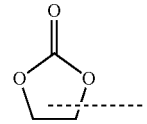 (2)

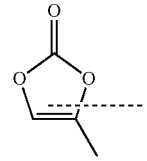 (3)

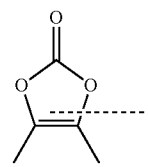 (4)

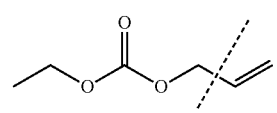 (5)

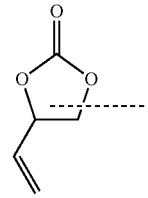 (6)

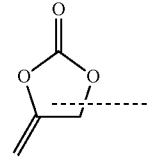 (7)

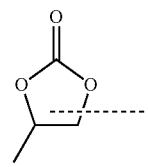 (8)

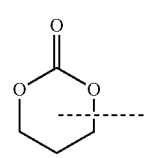 (9)

-continued

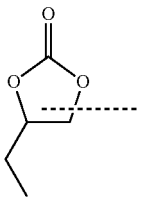 (10)

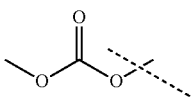 (11)

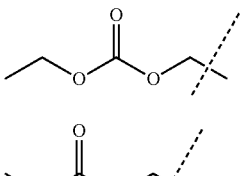 (12)

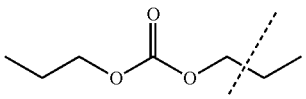 (13)

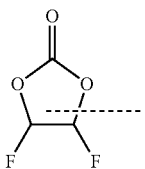 (14)

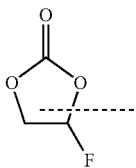 (15)

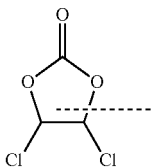 (16)

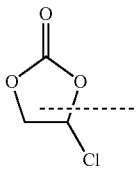 (17)

where the dashed line represents a covalent bond between the organic carbonate group and the hydrocarbylene bridge group or between the organic carbonate group and the heteroatom functional group.

E10. A composition according to any of the preceding embodiments where the functional group contains a heteroatom moiety selected from the group consisting of sulfonates, sulfates, sulfites, sulfones, sulfoxides or thio groups;

phosphates, phosphinates, phosphonates, phosphine oxides, phosphites, phosphonites, phosphinites or phosphines;

siloxanes, silyl ethers or silanes;

borates, boronic esters, borinic esters or boranes;

amines or amides; and bis-sulfonylimides;

for example, where the functional group contains a heteroatom moiety selected from the group consisting of
—S(O)$_2$O—, —OS(O)$_2$O—, —OS(O)O—, —S(O)$_2$—, —S(O)— or —S—;
—O—P(O)(OR)O—, —O—P(O)(R)—, —P(O)(OR)—, —O—P(O)(OR)—, —O—P(O)(R)—O—, —P(O)(R)—, —O—P(OR)—O—, —O—P(OR)—, —O—P(R)—O—, —P(OR)—, —O—P(R)— or —P(R)—;
—(R)(R)Si—O—Si(R)(R)—, —Si(R)(OR)—, —O—Si(R)(R)—, —Si(OR)(OR)—, —O—Si(R)(OR)—, —O—Si(R)(R)—O—, —Si(OR)(OR)—O—, —O—Si(R)(OR)—O— or —Si(R)(R)—;
—B(OR)—O—, —O—B(R)—O—, —B(R)—O—, —B(OR)—, —O—B(OR)—O— or —B(R)—;
—C(O)N(R)— or —N(R)—; and
—S(O)$_2$—NR'—S(O)$_2$—, where the open valences together are hydrocarbylene and form a ring; or one open valence is bonded to the bridge group or to the carbonate group and the other to a hydrogen or hydrocarbyl, R is independently hydrogen or hydrocarbyl and R' is hydrogen, hydrocarbyl or an alkali metal.

E11. A composition according to any of the preceding embodiments where the heteroatom functional group comprises S, for instance comprises a sulfonate, sulfate or sulfite moiety.

E12. A composition according to any of the preceding embodiments where the functional group is organic.

E13. A composition according to any of the preceding embodiments where the functional group is cyclic.

E14. A composition according to any of embodiments 1 to 12 where the heteroatom functional group is acyclic.

E15. A composition according to any of the preceding embodiments where the functional group is saturated.

E16. A composition according to any of embodiments 1 to 14 where the heteroatom functional group is unsaturated.

E17. A composition according to any of the preceding embodiments where the heteroatom functional group is selected from the group consisting of formulae (50)-(62)

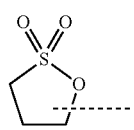 (50)

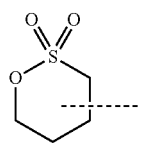 (51)

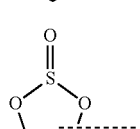 (52)

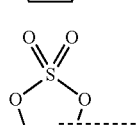 (53)

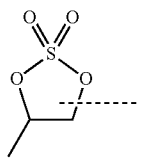
(54)

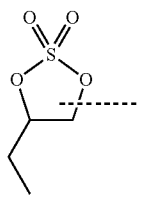
(55)

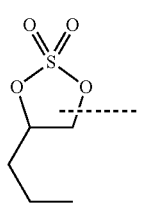
(56)

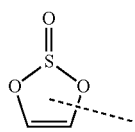
(57)

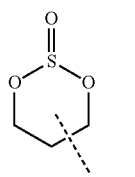
(58)

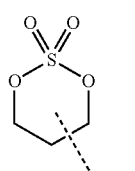
(59)

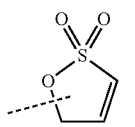
(60)

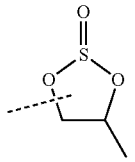
(61)

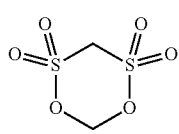
(62)

where the dashed line represents a covalent bond between the heteroatom functional group and the hydrocarbylene bridge group or a covalent bond between the heteroatom functional group and the organic carbonate group; or where the heteroatom functional group is selected from the group consisting of formulae (63)-(71)

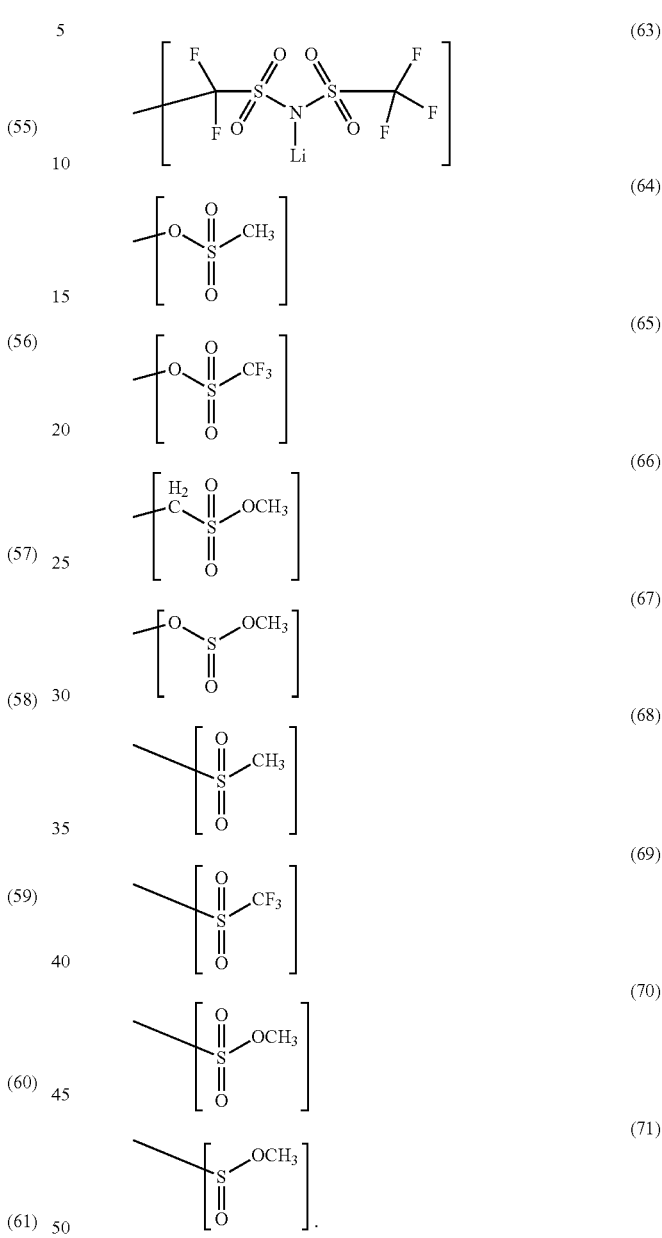

E18. A composition according to any of the preceding embodiments where m=1 and the bridge is an alkylene or an oxyalkylene, for example an alkylene containing from 1 to 12, from 1 to 8, from 1 to 6 or from 1 to 4 carbon atoms; or an oxyalkylene containing from 1 to 12 from 1 to 8, from 1 to 6 or from 1 to 4 carbon atoms and from 1 to 4 or from 1 to 3 oxygen atoms.

E19. A composition according to any of the preceding embodiments where m=2 and the bridge is an alkylene and forms a ring.

E20. A composition according to any of the preceding embodiments where the additive compound is present from about 0.01% to about 15% by weight, from about 0.1 to about 12%, from about 0.2 to about 10%, from about 0.3 to about 8%, from about 0.4 to about 7% or from about 0.5 to about 5% by weight, based on the total weight of the electrolyte composition; or where the additive is present at about 0.6, about 0.8, about 0.9, about 1.0, about 1.1, about 1.2, about 1.4, about 1.6, about 1.8, about 2.0, about 2.2, about 2.4, about 2.6, about 2.8, about 3.0, about 3.2, about 3.4, about 3.6, about 3.8, about 4.0, about 4.2, about 4.4, about 4.6, about 4.8 or about 5.0 percent by weight, based on the total weight of the electrolyte composition.

E21. A composition according to any of the preceding embodiments comprising one or more further additives selected from the group consisting of solid electrolyte interface improvers, cathode protection agents, $LiPF_6$ stabilizers, overcharge protectors, flame retardants, Li deposition improvers, solvation enhancers, corrosion inhibitors, wetting agents and viscosity adjusting agents.

E22. A composition according to any of the preceding embodiments further comprising one or more further additives selected from the group consisting of formulae (101) to (112)

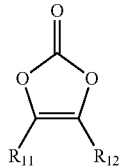 (101)

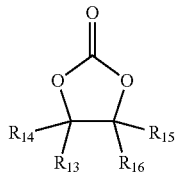 (102)

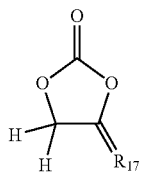 (103)

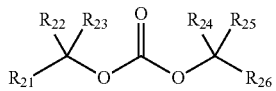 (104)

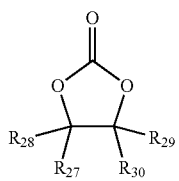 (105)

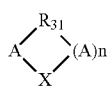 (106)

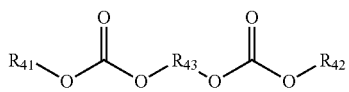 (107)

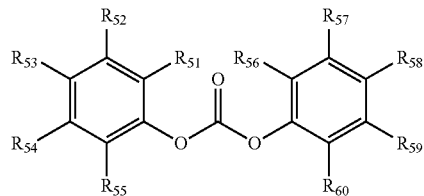 (108)

$Li_2PO_3F$ (109)
(lithium monofluorophosphate)

$Li_2PO_2F_2$ (110)
(lithium difluorophosphate)

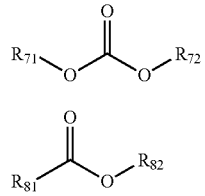 (111)

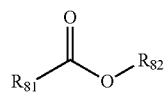 (112)

where
$R_{11}$ and $R_{12}$ are independently hydrogen, halogen, alkyl or haloalkyl;
$R_{13}$, $R_{14}$, $R_{15}$ and $R_{16}$ are independently hydrogen, halogen, alkyl, haloalkyl, vinyl or allyl, where at least one of $R_{13}$ to $R_{16}$ is vinyl or allyl;
$R_{17}$ is hydrogen or alkyl;
$R_{21}$ to $R_{26}$ are independently hydrogen, halogen, alkyl or haloalkyl, where at least one of $R_{21}$ to $R_{26}$ is halogen or haloalkyl;
$R_{27}$ to $R_{30}$ are independently hydrogen, halogen, alkyl or haloalkyl, where at least one of $R_{27}$ to $R_{30}$ is halogen or haloalkyl;
$R_{31}$ is an optionally substituted $C_1$-$C_6$alkylene, an optionally substituted $C_2$-$C_6$alkenylene or an optionally substituted cycloalkylene, A is C=O, SO or $SO_2$, n is 0 or 1 and X is oxygen (O) or sulfur (S);
$R_{41}$ and $R_{42}$ are independently an optionally substituted $C_1$-$C_6$alkyl, an optionally substituted $C_2$-$C_6$alkenyl or an optionally substituted $C_2$-$C_6$alkynyl and $R_{43}$ is an optionally substituted $C_1$-$C_6$alkylene, an optionally substituted $C_2$-$C_6$alkenylene, an optionally substituted $C_2$-$C_6$alkynylene or an optionally substituted cycloalkylene, where the substituent is for instance halogen or $C_1$-$C_6$alkyl;
$R_{51}$ to $R_{60}$ independently are an optionally substituted $C_1$-$C_{18}$alkyl, alkenyl, alkynyl, alkoxy or alkylamino, or two of $R_{51}$-$R_{60}$ together are hydrocarbylene, where the substituent is for instance halogen atom or $C_1$-$C_6$alkyl;
$R_{71}$ and $R_{72}$ are independently alkyl or haloalkyl; and
$R_{81}$ and $R_{82}$ are independently alkyl.

E23. A composition according to any of the preceding embodiments comprising one or more further additives selected from the group consisting of vinylene carbonate (1,3-dioxol-2-one), vinyl ethylene carbonate, monofluoroethylene carbonate, methylene ethylene carbonate, 1,3-propane sultone, 1,4-butyl sultone, prop-1-ene-1,3-sultone, 4-methyl-1,3,2-dioxathiolane-2-oxide and 1,5,2,4-dioxadithiane-2,2,4,4-tetraoxide.

E24. A composition according to any of the preceding embodiments comprising vinylene carbonate and/or propane sultone as a further additive.

E25. A composition according to any of the preceding embodiments comprising one or more further additives selected from the group consisting of ionic liquids.

A composition according to embodiment 25 where the ionic liquids comprise a cation selected from the group consisting of ammonium and phosphonium ions, for example imidazolium or pyrrolidinium ions, for instance 1-ethyl-3-methylimidazolium, 1-hexyl-3-methylimidazolium, 1-butyl-1-methylpyrrolidinium or trihexyl(tetradecyl)phosphonium.

E27. A composition according to embodiments 25 or 26 where the ionic liquids comprise an anion selected from the group consisting of carboxylates, imides, methides, borates, phosphates, phosphinates, phosphonates, sulfonates and aluminates.

E28. A composition according to any of embodiments 25 to 26 where the ionic liquids comprise a cation selected from the group consisting of formulae (a)-(h)

(a) $^+N(R)_4$ (b) $^+P(R)_4$ (c) 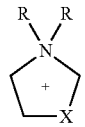

(d) 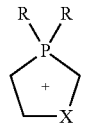

(e) 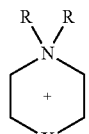

(f) 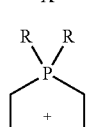

(g) 

(h) 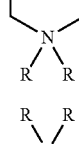

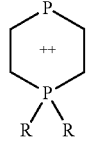

where
each R is independently H or $C_1$-$C_{16}$alkyl, for instance methyl, ethyl or propyl, X is $CH_2$, O, S or NR where R is H or $C_1$-$C_{16}$alkyl, for instance H, methyl, ethyl or propyl and comprise an anion selected from the group consisting of
$[F_zB(C_mF_{2m+1})_{4-z}]^-$,
$[F_yP(C_mF_{2m+1})_{6-y}]^-$,
$[(C_mF_{2m+1})_2P(O)O]^-$,
$[C_mF_{2m+1}P(O)O_2]^{2-}$,
$[O{-}C(O){-}C_mF_{2m+1}]^-$,
$[O{-}S(O)_2{-}C_mF_{2m+1}]^-$,
$[N(C(O){-}C_mF_{2m+1})_2]^-$,
$[N(S(O)_2{-}C_mF_{2m+1})_2]^-$,
$[N(C(O){-}C_mF_{2m+1})(S(O)_2{-}C_mF_{2m+1})]^-$,
$[N(C(O){-}C_mF_{2m+1})(C(O)F)]^-$,
$[N(S(O)_2{-}C_mF_{2m+1})(S(O)_2F)]^-$,
$[N(S(O)_2F)_2]^-$,
$[C(C(O){-}C_mF_{2m+1})_3]^-$,
$[C(S(O)_2{-}C_mF_{2m+1})_3]^-$,

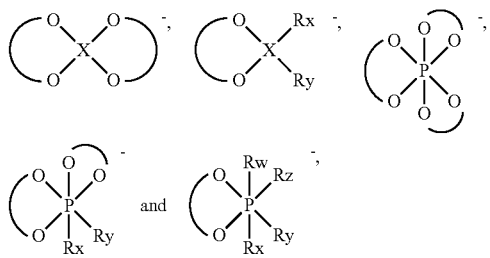

where
y is an integer of 1 to 5 and m is an integer of 1 to 8, for instance 1 to 4,
where any one $CF_2$ group may be replaced by O, $S(O)_2$, NR or $CH_2$,
where O⌒O is independently a bidentate group derived from the —OH groups of a 1,2- or 1,3-diol, a 1,2- or 1,3-dicarboxylic acid or from a 1,2- or 1,3-hydroxycarboxylic acid,
X is B or Al,
$R_w$, $R_x$, $R_y$, and $R_z$ are independently halogen, $C_1$-$C_{20}$perfluoroalkyl, $C_1$-$C_{20}$alkoxy, $C_1$-$C_{20}$alkoxy which is partly or fully fluorinated, $C_1$-$C_{20}$alkyl-COO, $C_1$-$C_{20}$alkyl-COO which is partly or fully fluorinated.

E29. A composition according to any of embodiments 25 to 28 where the ionic liquids comprise an anion selected from the group consisting of $F_2P(C_2F_5)_4{-}$, $F_3P(C_2F_5)_3{-}$, $F_4P(C_2F_5)_2{-}$, $F_2P(C_3F_7)_4{-}$, $F_3P(C_3F_7)_3{-}$, $F_4P(C_3F_7)_2{-}$, $F_2P(C_4F)_4{-}$, $F_3P(C_4F_9)_3{-}$, $F_4P(C_4F_9)_2{-}$, perfluoroalkylcarboxylate, perfluoroalkylsulfonate, bis(perfluoroalkylsulfonyl)imide, (perfluoroalkylsulfonyl)(perfluoroalkylcarboxyl)imide, tris(perfluoroalkylsulfonyl)methide, trifluoroacetate, trifluoromethanesulfonate (triflate), bis(trifluoromethylsulfonyl)imide, tris(trifluoromethylsulfonyl)methide, spiro-oxo borates and spiro-oxo phosphates, for example bisoxalatoborate (BOB), difluorooxalatoborate (dFOB), di(trifluoroacetato)oxalatoborate (d(Ac)OB), trisoxalatophosphate, tetrafluorooxalatophosphate or di(trifluoroacetato)oxalatoaluminate.

E30. A composition according to any of embodiments 20 to 28 where the further additives are present, in total, from about 0.01% to about 15%, from about 0.05 to about 10%, from about 0.1 to about 7% or from about 0.2 to about 5%, by weight, based on the total weight of the electrolyte composition, for instance, the further additives are present, in total, at a level of about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4 or about 2.5 percent by weight, based on the total weight of the electrolyte composition.

E31. A composition according to any of the preceding embodiments where the electrolyte composition comprises an organic solvent comprising one or more solvents selected from the group consisting of organic carbonates, sulfones, sulfoxides, esters, lactones, ethers and glymes.

E32. A composition according to embodiment 31 where the electrolyte composition contains a lithium salt; for example $LiPF_6$, $LiClO_4$, $LiN(CF_3SO_2)_2$, $LiAsF_6$, $LiCF_3SO_3$ or $LiBF_4$; for example where the lithium salts in total are present in the organic solvent at a level of from about 0.5 mol/L (M) to about 2.5 M, from about 0.5 M to about 2.0 M, from about 0.7 M to about 1.6 M or from about 0.8 M to about 1.2 M.

E33. An electrochemical device selected from the group consisting of primary lithium batteries, rechargeable lithium ion batteries, double layer capacitors, lithium ion capacitors, solar cells, electrochromic displays, sensors and biosensors, which device contains an electrolyte composition according to any of the preceding embodiments.

E34. A rechargeable lithium ion battery comprising at least one anode, at least one cathode, a separator disposed between the electrodes and an electrolyte composition according to any of embodiments 1 to 32 in contact with the electrodes.

Following are more embodiments of the invention.

E1. A multi-functional additive compound containing an SEI forming group and an SEI modifying group; for example a multi-functional additive containing an organic carbonate group covalently bonded to a heteroatom group; for example an additive of formula (SEI forming group)$_n$-(bridge)$_m$-(SEI modifying group)$_p$ where
bridge is a
m is 0, 1 or 2,
n is an integer from 1 to 10, for example from 1 to 5 or from 1 to 3,
p is an integer from 1 to 10, for example from 1 to 5 or from 1 to 3,
the SEI forming group comprises a chemical moiety capable of forming a solid electrolyte interface and
the SEI modifying group comprises a chemical moiety capable of modifying a solid electrolyte interface;
for example where the additive is of formula (organic carbonate group)$_n$-(bridge)$_m$-(heteroatom functional group)$_p$ where
the organic carbonate group contains a carbonate moiety and
the heteroatom functional group contains one or more heteroatoms selected from the group consisting of S, P, Si, B and N.

E2. A compound according to embodiment 1 where the SEI forming group is an organic carbonate group containing a moiety

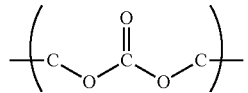

where the open valences together are hydrocarbylene and form a ring, which ring is bonded to the bridge group or heteroatom functional group; or one open valence is bonded to the bridge group or to the heteroatom functional group and the other to a hydrogen or hydrocarbyl, or both open valences are bonded to two bridging groups.

E3. A compound according to embodiment 2 where the organic carbonate group is cyclic.

E4. A compound according to embodiment 2 where the organic carbonate group is acyclic.

E5. A composition according to any of embodiments 2 to 4 where the organic carbonate group is unsaturated.

E6. A compound according to any of embodiments 2 to 4 where the organic carbonate group is saturated.

E7. A compound according to embodiment 2 where the organic carbonate group is cyclic and unsaturated.

E8. A compound according to any of the preceding embodiments where the organic carbonate group is selected from the group consisting of formulae (1)-(18)

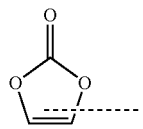 (1)

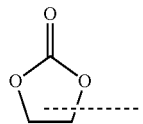 (2)

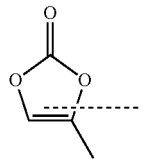 (3)

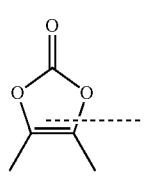 (4)

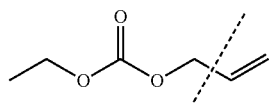 (5)

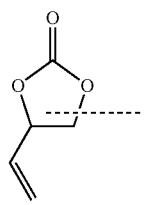 (6)

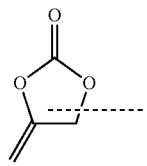 (7)

-continued (8) 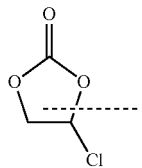

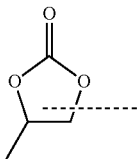

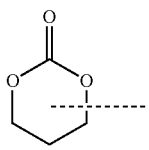

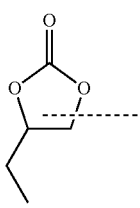

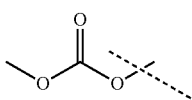

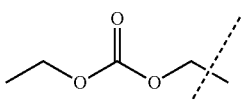

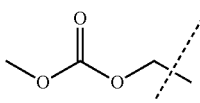

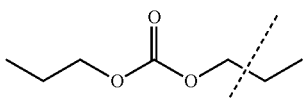

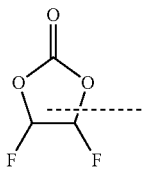

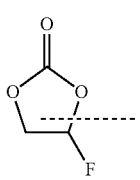

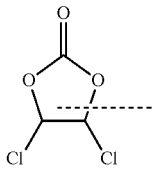

where the dashed line represents a covalent bond between the organic carbonate group and the hydrocarbylene bridge group or between the organic carbonate group and the heteroatom functional group.

E9. A compound according to any of the preceding embodiments where the functional group contains a heteroatom moiety selected from the group consisting of sulfonates, sulfates, sulfites, sulfones, sulfoxides or thio groups;

phosphates, phosphinates, phosphonates, phosphine oxides, phosphites, phosphonites, phosphinites or phosphines;

siloxanes, silyl ethers or silanes;

borates, boronic esters, borinic esters or boranes;

amines or amides; and bis-sulfonylimides;

for example, where the functional group contains a heteroatom moiety selected from the group consisting of —S(O)$_2$O—, —OS(O)$_2$O—, —OS(O)O—, —S(O)$_2$—, —S(O)— or —S—;

—O—P(O)(OR)O—, —O—P(O)(R)—, —P(O)(OR)—, —O—P(O)(OR)—, —O—P(O)(R)—O—, —P(O)(R)—, —O—P(OR)—O—, —O—P(OR)—, —O—P(R)—O—, —P(OR)—, —O—P(R)— or —P(R)—;

—(R)(R)Si—O—Si(R)(R)—, —Si(R)(OR)—, —O—Si(R)(R)—, —Si(OR)(OR)—, —O—Si(R)(OR)—, —O—Si(R)(R)—O—, —Si(OR)(OR)—O—, —O—Si(R)(OR)—O— or —Si(R)(R)—;

—B(OR)—O—, —O—B(R)—O—, —B(R)—O—, —B(OR)—, —O—B(OR)—O— or —B(R)—;

—C(O)N(R)— or —N(R)—; and

—S(O)$_2$—NR'—S(O)$_2$—, where the open valences together are hydrocarbylene and form a ring; or one open valence is bonded to the bridge group or to the carbonate group and the other to a hydrogen or hydrocarbyl, R is independently hydrogen or hydrocarbyl and R' is hydrogen, hydrocarbyl or an alkali metal.

E10. A compound according to any of the preceding embodiments where the heteroatom functional group comprises S, for instance comprises a sulfonate, sulfate or sulfite moiety.

E11. A compound according to any of the preceding embodiments where the functional group is organic.

E12. A compound according to any of the preceding embodiments where the functional group is cyclic.

E13. A compound according to any of embodiments 1 to 11 where the heteroatom functional group is acyclic.

E14. A compound according to any of the preceding embodiments where the functional group is saturated.

E15. A compound according to any of embodiments 1 to 13 where the heteroatom functional group is unsaturated.

E16. A compound according to any of the preceding embodiments where the heteroatom functional group is selected from the group consisting of formulae (50)-(62)

(50) 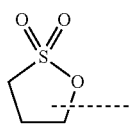
(51) 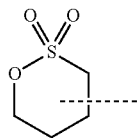
(52) 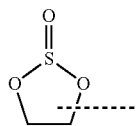
(53) 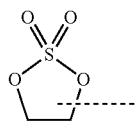
(54) 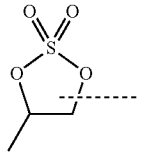
(55) 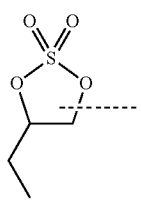
(56) 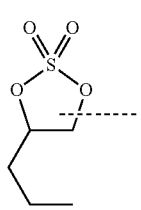
(57) 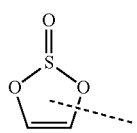
(58) 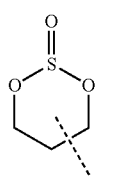
(59) 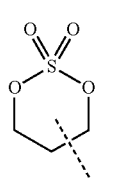
(60) 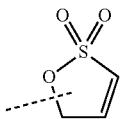
(61) 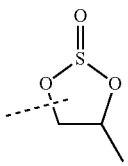
(62) 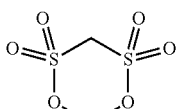
where the dashed line represents a covalent bond between the heteroatom functional group and the hydrocarbylene bridge group or a covalent bond between the heteroatom functional group and the organic carbonate group; or where the heteroatom functional group is selected from the group consisting of formulae (63)-(71)
(63) 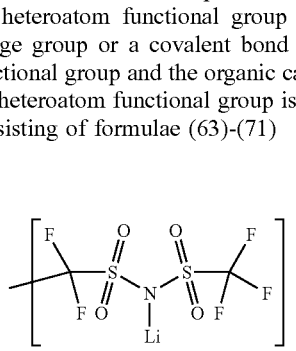
(64) 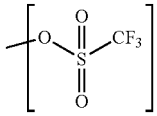
(65) 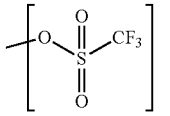
(66) 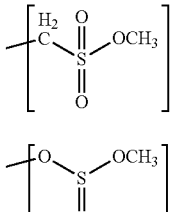
(67)
(68) 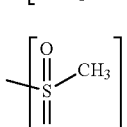
(69) 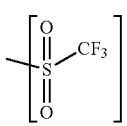

-continued

(70)
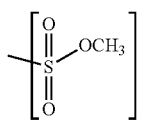

(71)
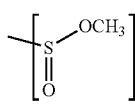

E17. A compound according to any of the preceding embodiments where m=1 and the bridge is an alkylene or an oxyalkylene, for example an alkylene containing from 1 to 12, from 1 to 8, from 1 to 6 or from 1 to 4 carbon atoms; or an oxyalkylene containing from 1 to 12 from 1 to 8, from 1 to 6 or from 1 to 4 carbon atoms and from 1 to 4 or from 1 to 3 oxygen atoms.

E18. An electrolyte composition comprising a multifunctional compound according to any of embodiments 1 to 17.

E19. An electrochemical device comprising the electrolyte composition of embodiment 18; for example an electrochemical device selected from the group consisting of primary lithium batteries, rechargeable lithium batteries, double layer capacitors, lithium ion capacitors, solar cells, electrochromic displays, sensors and biosensors.

E20. A rechargeable lithium ion battery comprising at least one anode, at least one cathode, a separator disposed between the electrodes and an electrolyte composition according to embodiment 18 in contact with the electrodes.

Example 1 Preparation of Additives

1. Preparation of Methyl Vinyl Carbonate Bonded to a Methyl Sulfite Group Through a Methylene Bridge.

4-Chloromethyl-5-methyl vinylene carbonate (Sigma Aldrich) is reacted with sodium sulfite to prepare the corresponding 4-sulfite-methyl salt. The salt is reacted with methyl trifluromethane sulfonate (methyl triflate) to prepare the product:

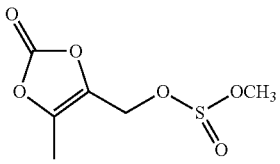

Alternatively, thionyl chloride is reacted with methanol to prepare methyl chlorosulfinate. Methyl chlorosulfinate is reacted with 4-hydroxymethyl ethylene carbonate (Sigma Aldrich) to prepare the product.

2. Preparation of Methyl Vinyl Carbonate Bonded to Trifluoromethane Sulfonate Through a Methylene Bridge.

4-Chloromethyl-5-methyl vinylene carbonate (Sigma Aldrich) is reacted with triflic acid to prepare:

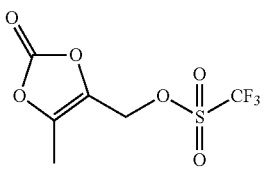 [SMILES: Cc1oc(=O)oc1COS(=O)(=O)C(F)(F)F]

Alternatively, 4-hydroxymethyl ethylene carbonate (Sigma Aldrich) is reacted with trifluoromethanesulfonyl chloride to prepare the product.

3. Preparation of Methyl Vinyl Carbonate Bonded to Methyl Sulfonate Through an Oxyalkylene Bridge.

4-Chloromethyl-5-methyl vinylene carbonate (Sigma Aldrich) is reacted with ethylene glycol to prepare the corresponding glycol ether. The ether is reacted with methane sulfonyl chloride to prepare:

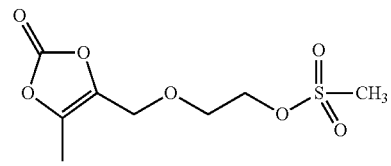 [SMILES: Cc1oc(=O)oc1COCCOS(C)(=O)=O]

4. Preparation of Methyl Vinyl Carbonate Bonded to Trifluromethane Sulfonate Through an Oxyalkylene Bridge.

4-Chloromethyl-5-methyl vinylene carbonate (Sigma Aldrich) is reacted with ethylene glycol to prepare the corresponding glycol ether. The ether is reacted with trifluoromethane sulfonyl chloride to prepare:

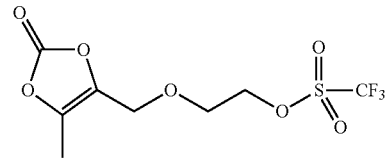 [SMILES: Cc1oc(=O)oc1COCCOS(=O)(=O)C(F)(F)F]

5. Preparation of Ethylene Carbonate Bonded to Methyl Sulfonate Through an Oxyalkylene Bridge.

4-Hydroxymethyl ethylene carbonate (Sigma Aldrich) is reacted with 1,3-propane sultone to produce the sulfonate salt. The sulfonate salt is reacted with methyl triflate to prepare:

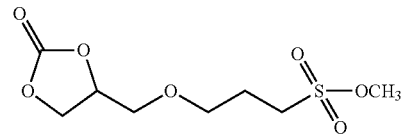 [SMILES: COS(=O)(=O)CCCOCC1COC(=O)O1]

6. Preparation of Vinylene Carbonate Propene Sultone Adduct Through Two Covalent Bonded methylene groups.

Di-methylene ethylene carbonate (BASF) and propene sultone (commercially available) undergoes Diels-Alder addition to form the vinylene carbonate-Propane sultone adduct compound through two covalent bonded methylene group.

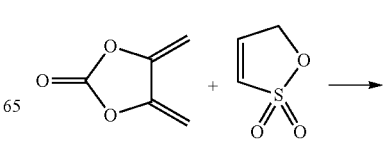

-continued

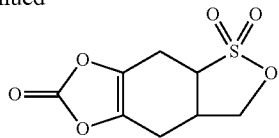

Example 2 Lithium Ion Battery

Six separate electrolyte compositions are prepared with a 1:1:1 weight ratio of ethylmethyl carbonate (EMC), diethyl carbonate (DEC) and ethylene carbonate (EC) solvent containing 1 mol/L $LiPF_6$. The electrolyte compositions further respectively contain 1 weight percent of the additives of Example 1 (1-6 compounds), based on the total weight of the composition. Each of the 6 electrolyte compositions are tested in a lithium ion battery.

Cathode active material slurry is prepared by dispersing NCM(111) cathode active material, polyvinylidene fluoride binder and carbon conductive material in N-methyl-2-pyrrolidone solvent in a weight ratio of 90:5:5. The cathode is formed by coating the slurry onto 20 micron thick aluminum foil followed by drying and rolling the coated foil. Anode active material slurry is prepared by mixing synthetic graphite active material, styrene-butadiene rubber binder and carboxymethylcellulose thickener in a weight ratio of 96:2:2 and dispersing the mixture in water. The anode slurry is coated onto a 10 pm thick copper foil followed by drying and rolling the coated foil. A 16 pm thick polyethylene separator is placed between the electrodes and the assembly is wound and pressurized. The assembly is inserted into an open end of a prismatic aluminum can. Electrolyte compositions are injected into the can to complete preparation of the lithium ion cells.

Cycle Life.

Cycle life testing is conducted at room temperature and 45° C., by repeatedly charging and discharging the prepared cells according to the following schedule: charging the aforementioned initially charged/discharged battery at a constant current rate of 1 C to 4.2 V and then charged at a constant voltage of 4.2 V until the current is less than or equal to 5% of the 1 C current. The battery is then discharged at a constant current rate of 1 C until the cut-off voltage 2.8 V is reached.

Initial charging and discharging of the aforementioned assembled battery is performed to condition the cells according to the constant current/voltage charging and the constant current discharging method in a room temperature atmosphere. The battery is then discharged and charged with normal constant-current constant voltage profile. During charge, after reaching 4.2 V, the battery is continually charged at a constant voltage of 4.2 V until the charging current is less than or equal to 5% of the nominal 1 C current. Then the battery is discharged at a constant current rate of 1 C until the cut-off voltage 2.8 V reached. Standard capacity of a non-aqueous electrolyte secondary battery is 1500 mAh.

High temperature storage test is conducted by first charging the aforementioned initially charged/discharged battery under room temperature at a constant current rate of 1 C to 4.2 V and then charged at a constant voltage of 4.2 V until the current is less than or equal to 5% of the nominal 1 C current. The battery is then discharged at a constant current rate of 1 C until the cut-off voltage 2.8 V is reached. This discharge capacity is noted as the starting discharge capacity. The battery is then charged again under room temperature at a constant current rate of 1 C to 4.2 V and then is charged at a constant voltage of 4.2 V until the current is less than or equal to 5% of 1 C current. The fully charged battery is stored at oven set at constant temperature of 60° C. for four weeks. Volume of the battery is measured before and after the storage when the battery is at both the storage temperature and room temperature. The retained discharge capacity is obtained by constant current discharge at C rate under room temperature after the storage. The recoverable discharge capacity is obtained by continuing cycling the battery the same way as before the storage test.

The volume increase rate is:

(Volume after the storage−volume before the storage)/volume before the storage×100%

The capacity retention ratio is:

retained capacity after the storage/starting capacity× 100%

The recoverable capacity ratio is:

Recoverable capacity after the storage/starting discharge capacity×100%

The invention claimed is:

1. An electrolyte composition, which composition comprises a multi-functional additive compound containing an SEI forming group and an SEI modifying group (SEI forming group)$_n$-(bridge)$_m$-(SEI modifying group)$_p$ wherein
bridge is a hydrocarbylene,
m is 0, 1 or 2,
n is an integer from 1 to 5,
p is an integer from 1 to 5,
(A) the SEI forming group is an organic carbonate group, and the SEI modifying group is a heteroatom functional group, the organic carbonate group is selected from the group consisting of the following formulae,

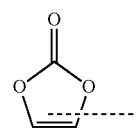

(1)

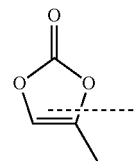

(3)

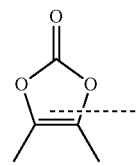

(4)

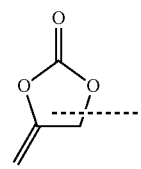

(7)

-continued

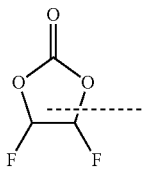
(15)

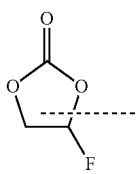
(16)

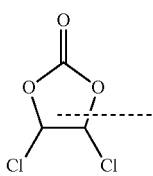
(17)

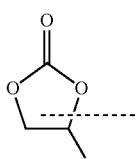
(18)

wherein the dashed line represents a covalent bond between the organic carbonate group and the hydrocarbylene bridge group(s) or between the organic carbonate group and the heteroatom functional group, and the heteroatom functional group contains one heteroatom selected from the group consisting of S, P, Si and B, or the heteroatom functional group contains more than one heteroatoms selected from the group consisting of S, P, Si, B and N, wherein the heteroatom functional group containing heteroatom S contains a heteroatom moiety selected from the group consisting of —S(O)$_2$O—, —OS(O)$_2$O— or —OS(O)O—;

or (B) the SEI forming group is an organic carbonate group, and
the SEI modifying group is a heteroatom functional group, the heteroatom functional group is selected from the group consisting of
sulfates or sulfites; and
borates, boronic esters or borinic esters.

2. A composition according to claim 1, wherein the organic carbonate group contains a carbonate moiety

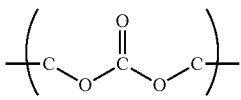

wherein (A) or (B), the open valences together are hydrocarbylene and form a ring, which ring is bonded to the bridge group(s) or to the heteroatom functional group; or (B), one open valence is bonded to the bridge group or to the heteroatom functional group and the other to a hydrogen or hydrocarbyl or both open valences are bonded to two bridging groups.

3. A composition according to claim 1, wherein (B) the organic carbonate group is cyclic.

4. A composition according to claim 1, wherein (A) or (B) the organic carbonate group is unsaturated.

5. A composition according to claim 1, wherein (A) or (B) the organic carbonate group is cyclic and unsaturated.

6. A composition according to claim 1, wherein (B) the SEI modifying group is a heteroatom functional group, the heteroatom functional group is selected from the group consisting of
sulfates or sulfites;
borates, boronic esters or borinic esters; and
the SEI forming group is an organic carbonate group, the organic carbonate group is selected from the group consisting of formulae (1)-(18)

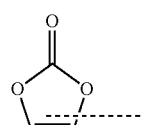
(1)

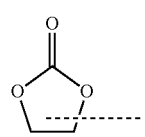
(2)

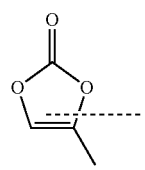
(3)

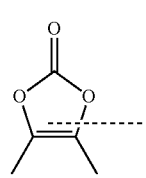
(4)

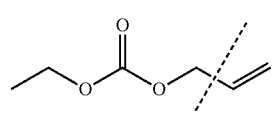
(5)

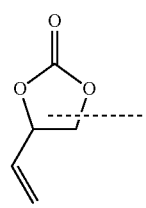
(6)

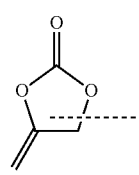
(7)

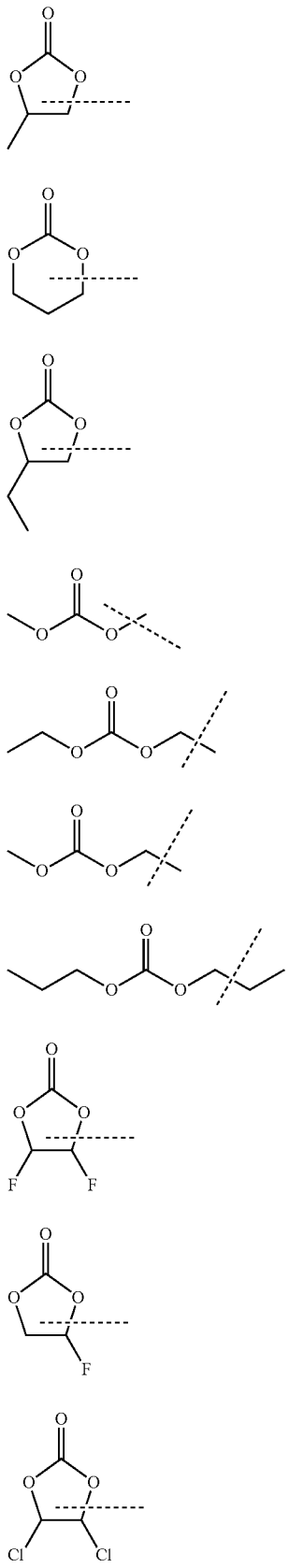

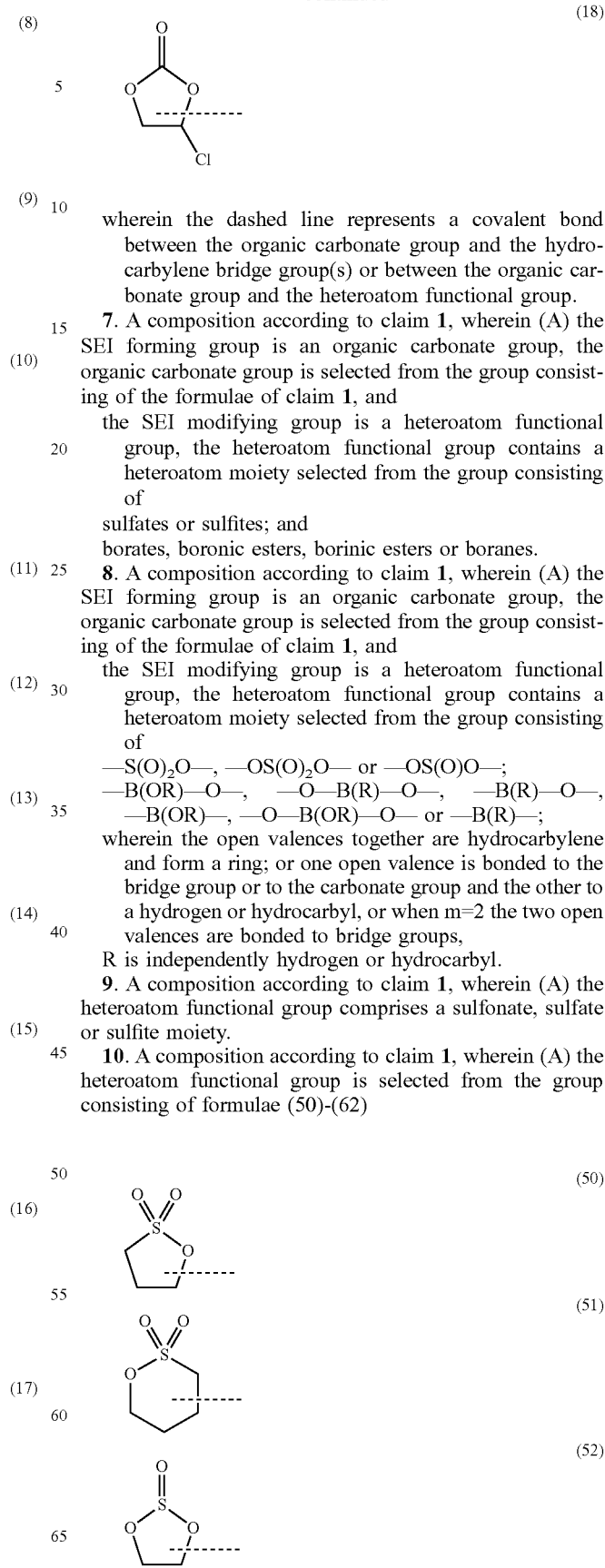

wherein the dashed line represents a covalent bond between the organic carbonate group and the hydrocarbylene bridge group(s) or between the organic carbonate group and the heteroatom functional group.

7. A composition according to claim 1, wherein (A) the SEI forming group is an organic carbonate group, the organic carbonate group is selected from the group consisting of the formulae of claim 1, and the SEI modifying group is a heteroatom functional group, the heteroatom functional group contains a heteroatom moiety selected from the group consisting of sulfates or sulfites; and borates, boronic esters, borinic esters or boranes.

8. A composition according to claim 1, wherein (A) the SEI forming group is an organic carbonate group, the organic carbonate group is selected from the group consisting of the formulae of claim 1, and the SEI modifying group is a heteroatom functional group, the heteroatom functional group contains a heteroatom moiety selected from the group consisting of —S(O)$_2$O—, —OS(O)$_2$O— or —OS(O)O—;

—B(OR)—O—, —O—B(R)—O—, —B(R)—O—, —B(OR)—, —O—B(OR)—O— or —B(R)—;

wherein the open valences together are hydrocarbylene and form a ring; or one open valence is bonded to the bridge group or to the carbonate group and the other to a hydrogen or hydrocarbyl, or when m=2 the two open valences are bonded to bridge groups, R is independently hydrogen or hydrocarbyl.

9. A composition according to claim 1, wherein (A) the heteroatom functional group comprises a sulfonate, sulfate or sulfite moiety.

10. A composition according to claim 1, wherein (A) the heteroatom functional group is selected from the group consisting of formulae (50)-(62)

-continued

(53) 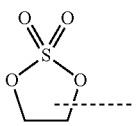

(54) 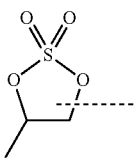

(55) 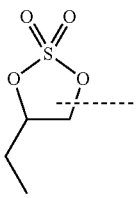

(56) 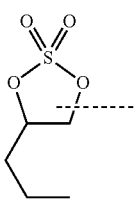

(57) 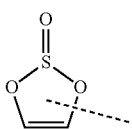

(58) 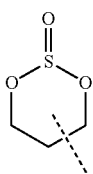

(59) 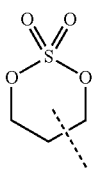

(60) 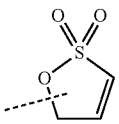

(61) 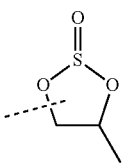

-continued

(62) 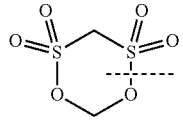

wherein the dashed line represents a covalent bond between the heteroatom functional group and the hydrocarbylene bridge group(s) or a covalent bond between the heteroatom functional group and the organic carbonate group; or wherein the heteroatom functional group is selected from the group consisting of formulae (63)-(67) and (70)

(63) 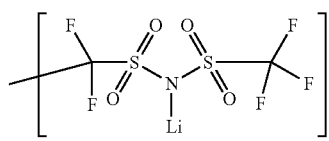

(64) 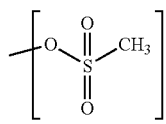

(65) 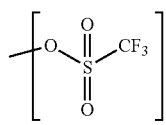

(66) 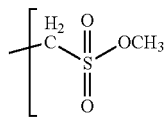

(67) 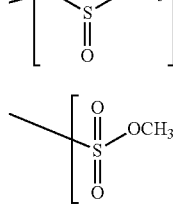

(70)

11. A composition according to claim 1, wherein m=1 and the bridge is an alkylene group or an oxyalkylene group.

12. A composition according to claim 1, wherein m=2 and the bridges are alkylene groups or oxyalkylene groups.

13. A composition according to claim 1, wherein the additive compound is present from about 0.01% to about 15% by weight, based on the total weight of the electrolyte composition.

14. A composition according to claim 1, comprising one or more further additives selected from the group consisting of solid electrolyte interface improvers, cathode protection agents, LiPF$_6$ stabilizers, overcharge protectors, flame retardants, Li deposition improvers, solvation enhancers, corrosion inhibitors, wetting agents and viscosity adjusting agents.

15. A composition according to claim 1, comprising one or more further additives selected from the group consisting of formulae (101) to (112)

(101)

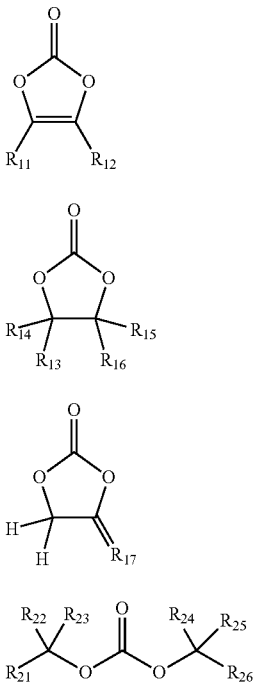

(102)

(103)

(104)

(105)

(106)

(107)

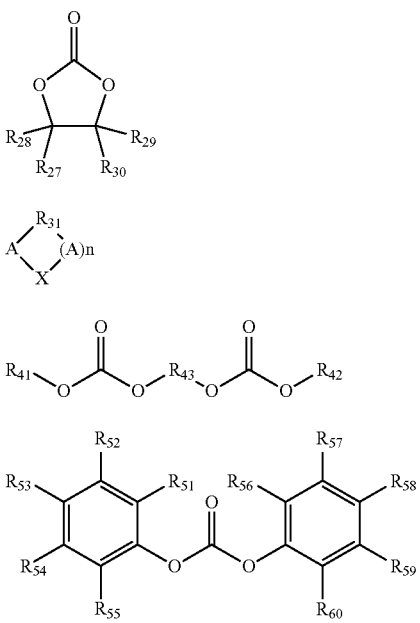

(108)

(109) Li$_2$PO$_3$F (lithium monofluorophosphate)

(110) LiPO$_2$F$_2$ (lithium difluorophosphate)

(111)

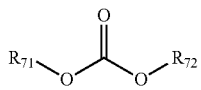

(112)

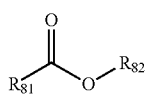

wherein $R_{11}$ and $R_{12}$ are independently hydrogen, halogen, alkyl or haloalkyl;

$R_{13}$, $R_{14}$, $R_{15}$ and $R_{16}$ are independently hydrogen, halogen, alkyl, haloalkyl, vinyl or allyl, wherein at least one of $R_{13}$ to $R_{16}$ is vinyl or allyl;

$R_{17}$ is hydrogen or alkyl;

$R_{21}$ to $R_{26}$ are independently hydrogen, halogen, alkyl or haloalkyl, wherein at least one of $R_{21}$ to $R_{26}$ is halogen or haloalkyl;

$R_{27}$ to $R_{30}$ are independently hydrogen, halogen, alkyl or haloalkyl, wherein at least one of $R_{27}$ to $R_{30}$ is halogen or haloalkyl;

$R_{31}$ is an optionally substituted $C_1$-$C_6$alkylene, an optionally substituted $C_2$-$C_6$alkenylene or an optionally substituted cycloalkylene, A is C=O, SO or SO$_2$, n is 0 or 1 and X is oxygen (O) or sulfur (S);

$R_{41}$ and $R_{42}$ are independently an optionally substituted $C_1$-$C_6$alkyl, an optionally substituted $C_2$-$C_6$alkenyl or an optionally substituted $C_2$-$C_6$alkynyl and $R_{43}$ is an optionally substituted $C_1$-$C_6$alkylene, an optionally substituted $C_2$-$C_6$alkenylene, an optionally substituted $C_2$-$C_6$alkynylene or an optionally substituted cycloalkylene, wherein the substituent is halogen or $C_1$-$C_6$alkyl;

$R_{51}$ to $R_{60}$ independently are an optionally substituted $C_1$-$C_{18}$alkyl, alkenyl, alkynyl, alkoxy or alkylamino, or two of $R_{51}$-$R_{60}$ together are hydrocarbylene, wherein the substituent is halogen atom or $C_1$-$C_6$alkyl;

$R_{71}$ and $R_{72}$ are independently alkyl or haloalkyl; and $R_{81}$ and $R_{82}$ are independently alkyl.

16. A composition according to claim 1, comprising one or more further additives selected from the group consisting of vinylene carbonate (1,3-dioxol-2-one), vinyl ethylene carbonate, monofluoroethylene carbonate, methylene ethylene carbonate, 1,3-propane sultone, 1,4-butyl sultone, prop-1-ene-1,3-sultone, 4-methyl-1,3,2-dioxathiolane-2-oxide and 1,5,2,4-dioxadithiane-2,2,4,4-tetraoxide.

17. An electrochemical device selected from the group consisting of primary lithium batteries, rechargeable lithium ion batteries, double layer capacitors, lithium ion capacitors, solar cells, electrochromic displays, sensors and biosensors, which device contains an electrolyte composition according to claim 1.

18. A rechargeable lithium ion battery comprising at least one anode, at least one cathode, a separator disposed between the electrodes and an electrolyte composition according to claim 1 in contact with the electrodes.

19. A composition according to claim 1, wherein the organic carbonate group is saturated.

20. A composition according to claim 1, wherein (B) the heteroatom functional group is selected from the group consisting of formulae (52)-(59) and (61), (52)

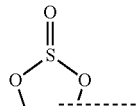

(53)

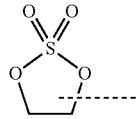

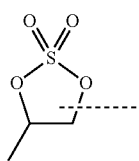
(54)
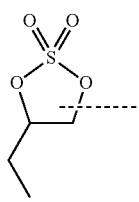
(55)
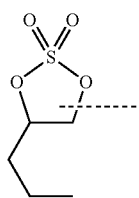
(56)
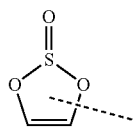
(57)
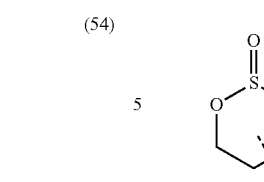
(58)
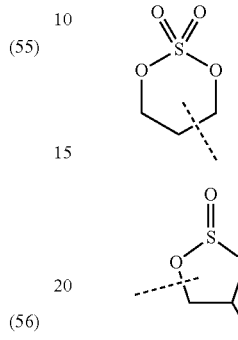
(59)
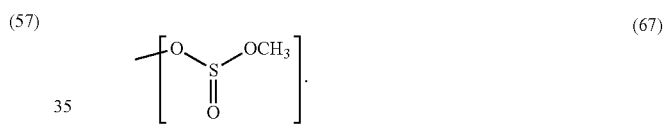
(61)
wherein the dashed line represents a covalent bond between the heteroatom functional group and the hydrocarbylene bridge group(s) or a covalent bond between the heteroatom functional group and the organic carbonate group; or wherein the heteroatom functional group is formula (67),
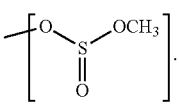
(67)
\* \* \* \* \*